(12) United States Patent
Van Kruchten et al.

(10) Patent No.: US 11,807,594 B2
(45) Date of Patent: Nov. 7, 2023

(54) PROCESS FOR THE PREPARATION OF ETHYLENE GLYCOL

(71) Applicant: SHELL OIL COMPANY, Houston, TX (US)

(72) Inventors: Eugene Marie Godfried Andre Van Kruchten, Amsterdam (NL); Petrus Johannes Gerardus Boons, Singapore (SG)

(73) Assignee: SHELL USA, INC., Houston, TX (US)

( * ) Notice: Subject to any disclaimer, the term of this patent is extended or adjusted under 35 U.S.C. 154(b) by 232 days.

(21) Appl. No.: 17/311,871

(22) PCT Filed: Dec. 6, 2019

(86) PCT No.: PCT/EP2019/083948
§ 371 (c)(1),
(2) Date: Jun. 8, 2021

(87) PCT Pub. No.: WO2020/120305
PCT Pub. Date: Jun. 18, 2020

(65) Prior Publication Data
US 2022/0024841 A1    Jan. 27, 2022

(30) Foreign Application Priority Data
Dec. 10, 2018 (EP) .................................... 18211334

(51) Int. Cl.
*C07C 29/12* (2006.01)
*C07C 31/20* (2006.01)
(Continued)

(52) U.S. Cl.
CPC ............ *C07C 29/12* (2013.01); *C07C 29/106* (2013.01); *C07C 31/202* (2013.01); *C07D 317/38* (2013.01); *C07D 301/00* (2013.01)

(58) Field of Classification Search
CPC ...... C07C 29/12; C07C 29/106; C07C 31/202; C07D 317/38; C07D 301/00
See application file for complete search history.

(56) References Cited

U.S. PATENT DOCUMENTS

| 4,283,580 A | 8/1981 | Odanaka et al. |
| 4,400,559 A | 8/1983 | Bhise |

(Continued)

FOREIGN PATENT DOCUMENTS

| CN | 1745051 A | 5/2007 |
| EP | 0776890 A2 | 6/1997 |

(Continued)

OTHER PUBLICATIONS

International Search Report and Written Opinion received for PCT Patent Application No. PCT/EP2019/083948, dated Mar. 3, 2020, 08 pages.

(Continued)

*Primary Examiner* — Yate' K Cutliff
(74) *Attorney, Agent, or Firm* — SHELL USA, INC.

(57) ABSTRACT

The invention relates to a process for the preparation of ethylene glycol from ethylene, which comprises contacting the carbon dioxide stream resulting from hydrolysing ethylene carbonate, or the condensate stream resulting from condensing said carbon dioxide stream, or the waste water stream resulting from removing water from the ethylene glycol stream, such stream comprising water, 2-chloroethanol and ethylene glycol and additionally comprising 2-iodoethanol or 2-bromoethanol, with an alkali metal containing basic compound to form a mixture comprising water, 2-chloroethanol and ethylene glycol and additionally comprising alkali metal iodide or alkali metal bromide which mixture is dehydrated.

8 Claims, 3 Drawing Sheets

(51) Int. Cl.
*C07C 29/10* (2006.01)
*C07D 317/38* (2006.01)
*C07D 301/00* (2006.01)

(56) References Cited

U.S. PATENT DOCUMENTS

| | | |
|---|---|---|
| 4,508,927 A | 4/1985 | Bhise et al. |
| 4,831,196 A | 5/1989 | Buonicore et al. |
| 6,380,419 B2 | 4/2002 | Kawabe |
| 8,802,900 B2 * | 8/2014 | Smaardijk ............... C07C 29/09 568/858 |
| 2004/0267058 A1 | 12/2004 | Harmsen et al. |
| 2012/0136178 A1 | 5/2012 | Smaardijk et al. |

FOREIGN PATENT DOCUMENTS

| | | | |
|---|---|---|---|
| JP | H09208509 A | 8/1997 | |
| SG | 185059 * | 12/2012 | ............. C07C 29/10 |
| SG | 185059 A1 * | 12/2012 | ............. C07C 29/10 |
| WO | 2009021830 A1 | 2/2009 | |
| WO | 2009124987 A1 | 10/2009 | |
| WO | 2009140319 A1 | 11/2009 | |
| WO | 2011136127 A1 | 11/2011 | |

OTHER PUBLICATIONS

International Search Report and Written Opinion received for PCT Patent Application No. PCT/EP2011/071279, dated Feb. 9, 2012, 08 pages.

* cited by examiner

PROCESS FOR THE PREPARATION OF ETHYLENE GLYCOL

CROSS REFERENCE TO RELATED APPLICATIONS

This is a National stage application of International application No. PCT/EP2019/083948, filed 06 Dec. 2019, which claims priority of European application No. 18211334.0, filed 10 Dec. 2018, which is incorporated herein by reference in its entirety.

FIELD OF THE INVENTION

The present invention relates to a process for the preparation of ethylene glycol from ethylene.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide, which is in turn prepared from ethylene. In order to produce ethylene oxide, ethylene and oxygen are passed over an epoxidation catalyst, for example, a silver oxide catalyst, typically at pressures of 10-30 bar and temperatures of 200-300° C., producing a product stream comprising ethylene oxide, carbon dioxide, ethylene, oxygen and water. The amount of ethylene oxide in the product stream is usually between about 0.5 and 10 weight percent. The product stream is supplied to an ethylene oxide absorber and the ethylene oxide is absorbed by a recirculating solvent (absorbent) stream containing mostly water. After absorption, the aqueous ethylene oxide stream is sent to a stripper in order to separate the ethylene oxide. The ethylene oxide leaves the top of the stripper as a concentrated aqueous ethylene oxide stream.

In one well-known process, ethylene oxide is then catalytically reacted with carbon dioxide to produce ethylene carbonate (carboxylation). The ethylene carbonate is subsequently hydrolysed to provide ethylene glycol and carbon dioxide. Reaction via ethylene carbonate significantly improves the selectivity of ethylene oxide conversion to monoethylene glycol compared to the known process wherein ethylene oxide is reacted with a large excess of water to form ethylene glycol in a non-catalytic process.

The catalytic reaction of ethylene to ethylene oxide usually takes place in the presence of a moderator, which controls the performance of the epoxidation catalyst. Commonly used moderators include monochloroethane or dichloroethane. These organic chloride moderators are partially converted to other organic chloride compounds which end up in the ethylene oxide product stream that is supplied to the ethylene oxide absorber. These organic chloride compounds comprise 2-chloroethanol and chloromethyl dioxolane. These organic chloride compounds are partially absorbed in the ethylene oxide absorber, are present in the stream supplied to the ethylene oxide stripper and are present in the concentrated aqueous ethylene oxide stream taken from the top of the ethylene oxide stripper.

If the ethylene oxide is catalytically converted to monoethylene glycol via ethylene carbonate, as described above, the presence of the above organic chloride compounds in the concentrated ethylene oxide stream can lead to problems. These organic chloride compounds can react with hydrolysis catalysts such as potassium carbonate to produce inorganic chloride compounds (e.g. potassium chloride). Therefore, these organic chloride compounds can cause degradation of the hydrolysis catalysts and can also lead to a build-up of inorganic chloride. The inorganic chloride can start to precipitate and may cause chloride stress corrosion.

Indian patent application IN2012CN09850 discloses a process for the preparation of ethylene glycol from ethylene via hydrolysis of ethylene carbonate, as described above. In Example 2 of said IN2012CN09850, carbon dioxide gas, which was produced in a hydrolysis reactor, was cooled resulting in a condensation liquid (condensate) containing water, ethylene glycol, ethylene chlorohydrin (2-chloroethanol) and chloromethyl dioxolane. In Example 3 of said IN2012CN09850, together with the hydrolysis reactor liquid, said condensate from Example 2 was subjected to a distillation resulting in a top stream comprising water, ethylene chlorohydrin and chloromethyl dioxolane and an ethylene glycol bottom stream containing no organochlorine compound. The latter top stream can be discarded, so that the removed organic chloride compounds can no longer lead to the above-described problems.

In Example 3 of said IN2012CN09850, it is not disclosed explicitly at which positions of the distillation tower each of said condensation liquid and said hydrolysis reactor liquid are fed. However, in paragraph [0045] of said IN2012CN09850, it is disclosed that said condensation liquid should be fed to a distillation tower at a position which is above the position at which said hydrolysis reactor liquid is fed, to avoid any contact of said condensation liquid with the hydrolysis catalyst present in said hydrolysis reactor liquid.

However, in addition to above-mentioned organic chloride compounds that are removed in the process of said IN2012CN09850, organic iodide or bromide compounds may also be formed, such as for example 2-iodoethanol and 2-bromoethanol. This is caused by using iodide or bromide catalyst in carboxylation (making ethylene carbonate) and/or hydrolysis (of ethylene carbonate). Said 2-iodoethanol and 2-bromoethanol may be formed by reaction of iodide or bromide catalyst with ethylene oxide or ethylene carbonate, thereby resulting in loss of valuable iodide or bromide catalyst.

In said IN2012CN09850, it is indeed recognized that in the disclosed process valuable iodide and bromide catalyst gets lost. For in paragraph [0047] of said IN2012CN09850, it is disclosed that when halogen such as iodine or bromine derived from the carboxylation catalyst and/or the catalyst itself is/are removed in an accompanied manner with the removal of chlorine, it is preferable that the carboxylation catalyst and/or hydrolysis catalyst is/are additionally added, or hydrogen halide such as hydrogen iodide, hydrogen bromide or the like, which corresponds to the catalyst having been used, is added depending on the situation. Thus, said IN2012CN09850 suggests adding additional iodide or bromide catalyst to compensate for lost iodide or bromide catalyst.

It is an object of the present invention to provide a process for the preparation of ethylene glycol from ethylene via hydrolysis of ethylene carbonate, as described above, which remedies the above-described loss of iodide or bromide catalyst, thereby not having to add additional iodide or bromide catalyst or having to add substantially less additional iodide or bromide catalyst, and wherein at the same time the undesired organic chloride compounds can be removed and the recovery of ethylene glycol can be maximized.

SUMMARY OF THE INVENTION

Surprisingly it was found that the above-mentioned object may be achieved by contacting the carbon dioxide stream resulting from hydrolysing ethylene carbonate, or the condensate stream resulting from condensing said carbon dioxide stream, or the waste water stream resulting from removing water from the ethylene glycol stream, such stream comprising water, 2-chloroethanol and ethylene glycol and additionally comprising 2-iodoethanol or 2-bromoethanol, with an alkali metal containing basic compound to form a mixture comprising water, 2-chloroethanol and ethylene glycol and additionally comprising alkali metal iodide or alkali metal bromide which mixture is dehydrated.

Accordingly, the present invention relates to a process for the preparation of ethylene glycol from ethylene, said process comprising the steps of:

i) converting ethylene in the presence of oxygen, an epoxidation catalyst and a chloride moderator to ethylene oxide in an ethylene oxide reactor;

ii) absorbing the ethylene oxide in an aqueous absorbent and then stripping said absorbent to provide an aqueous ethylene oxide stream;

iii) converting the aqueous ethylene oxide stream in the presence of a catalyst and carbon dioxide in a carboxylation reactor to an ethylene carbonate stream;

iv) converting the ethylene carbonate stream in the presence of a catalyst in a hydrolysis reactor to an ethylene glycol stream and a carbon dioxide stream;

v) removing water from the ethylene glycol stream in a dehydration column to form a dehydrated ethylene glycol stream and a waste water stream;

vi) purifying the dehydrated ethylene glycol stream in a glycol distillation column to form a purified ethylene glycol product stream and a catalyst recycle stream;

wherein in step iii) and/or step iv) the catalyst is an iodide catalyst or a bromide catalyst;

the carbon dioxide stream resulting from step iv) comprises carbon dioxide, water, 2-chloroethanol and ethylene glycol and additionally comprises 2-iodoethanol or 2-bromoethanol and is condensed in a condenser to form a recycle carbon dioxide stream and a condensate stream; and the carbon dioxide stream resulting from step iv), or the condensate stream, or the waste water stream resulting from step v) is contacted with an alkali metal containing basic compound to convert 2-iodoethanol or 2-bromoethanol into alkali metal iodide or alkali metal bromide and the resulting mixture comprising water, 2-chloroethanol and ethylene glycol and additionally comprising alkali metal iodide or alkali metal bromide is dehydrated.

DETAILED DESCRIPTION OF THE INVENTION

Figure 1:
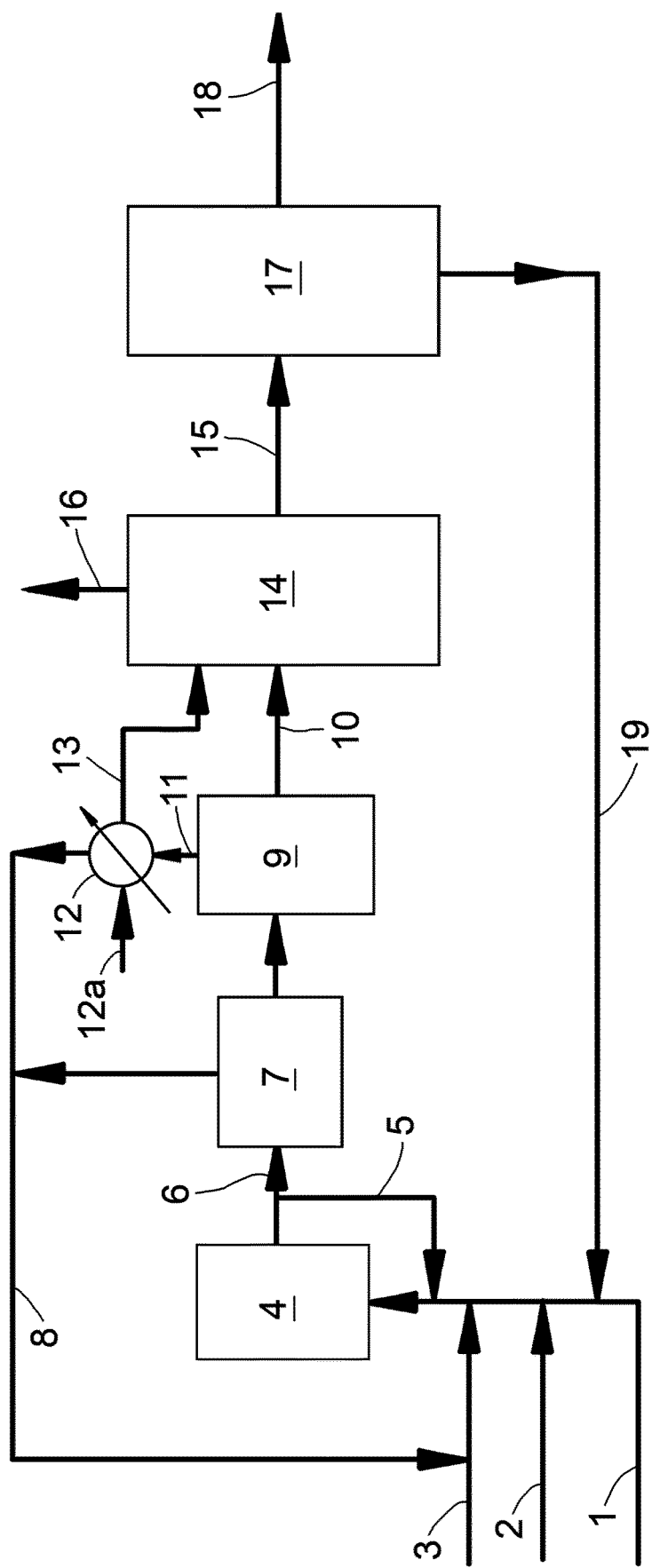
FIGS. 1 to 3 are schematic diagrams showing processes according to the invention.

The process of the present invention comprises various steps, as described hereinbelow. Said process may comprise one or more intermediate steps between these steps. Further, said process may comprise one or more additional steps preceding step i) and/or following step vi).

While the process of the present invention and mixtures or streams used in said process are described in terms of "comprising", "containing" or "including" one or more various described steps and components, respectively, they can also "consist essentially of" or "consist of" said one or more various described steps and components, respectively.

In the context of the present invention, in a case where a mixture, stream or catalyst comprises two or more components, these components are to be selected in an overall amount not to exceed 100%.

Within the present specification, "substantially no" means that no detectable amount of the component in question is present in the catalyst or composition.

Further, where upper and lower limits are quoted for a property then a range of values defined by a combination of any of the upper limits with any of the lower limits is also implied.

Within the present specification, "dehydration" of a stream or mixture comprising water and one or more other components refers to the removal of water from such stream or mixture. It does not refer to a chemical dehydration reaction involving the loss of a water molecule from a compound.

In ethylene oxide production step i) of the present process, a chloride moderator is used. In the present specification, "chloride moderator" refers to an organic compound containing one or more chlorine atoms. Said chloride moderator is further described hereinbelow in relation to step i). As described above, such chloride moderator is partially converted to 2-chloroethanol.

Further, in ethylene carbonate production step iii) and/or ethylene carbonate hydrolysis step iv) of the present process, the catalyst is an iodide catalyst or a bromide catalyst. In the present specification, "iodide catalyst" or "bromide catalyst" refers to a catalyst containing an iodide anion or bromide anion. Said catalysts are further described hereinbelow in relation to steps iii) and iv). As described above, 2-iodoethanol is formed by reaction of an iodide catalyst with ethylene oxide or ethylene carbonate and 2-bromoethanol is formed by reaction of a bromide catalyst with ethylene oxide or ethylene carbonate.

The above-mentioned 2-chloroethanol, 2-iodoethanol and 2-bromoethanol end up in the carbon dioxide stream resulting from ethylene carbonate hydrolysis step iv) of the present process. The carbon dioxide stream resulting from step iv) comprises carbon dioxide, water, 2-chloroethanol and ethylene glycol and additionally comprises 2-iodoethanol or 2-bromoethanol. In addition, the carbon dioxide stream resulting from step iv) may comprise chloromethyl dioxolane and iodomethyl dioxolane or bromomethyl dioxolane.

In the present process, above-mentioned carbon dioxide stream resulting from step iv) is condensed in a condenser to form a recycle carbon dioxide stream and a condensate stream. Further, the carbon dioxide stream resulting from step iv), or the condensate stream, or the waste water stream resulting from step v) is contacted with an alkali metal containing basic compound to convert 2-iodoethanol or 2-bromoethanol into alkali metal iodide or alkali metal bromide. Additionally, any iodomethyl dioxolane or bromomethyl dioxolane may also be converted into alkali metal iodide or alkali metal bromide upon contacting with said alkali metal containing basic compound. Advantageously, in the present invention, in such conversions additional valuable ethylene glycol is also formed which is recovered at a later stage. The resulting mixture comprising water, 2-chloroethanol and ethylene glycol and additionally comprising alkali metal iodide or alkali metal bromide is then dehydrated. Preferably, said mixture is dehydrated in step v). However, alternatively, said mixture may be dehydrated in another dehydration column, other than the dehydration column used in step v), to form a dehydrated ethylene glycol stream and a waste water stream, wherein the latter dehydrated ethylene glycol stream and the dehydrated ethylene glycol stream resulting from step v) may both be purified in step vi).

Advantageously, in the dehydration step of the present process, 2-chloroethanol is removed from the process together with water as part of a waste water stream. Ethylene glycol and alkali metal iodide or alkali metal bromide end up in a dehydrated ethylene glycol stream that is subsequently purified in step vi) to form a purified ethylene glycol product stream and a catalyst recycle stream. The latter catalyst recycle stream comprises said alkali metal iodide or bromide which may then advantageously be re-used as a catalyst in the present process. Furthermore, additional ethylene glycol originating from the condensate stream is advantageously recovered in the purified ethylene glycol product stream in step vi) of the present process.

In the present process, an alkali metal containing basic compound is used to convert 2-iodoethanol or 2-bromoethanol into alkali metal iodide or alkali metal bromide. The alkali metal in said alkali metal containing basic compound may be any alkali metal and may be lithium, sodium, potassium, rubidium or cesium, preferably lithium, sodium or potassium, more preferably sodium or potassium. Most preferably, said alkali metal is potassium.

Further, said alkali metal containing basic compound is a base which implies that the pH of an aqueous solution containing such basic compound is greater than 7, preferably at least 7.5, more preferably at least 8, more preferably at least 8.5, most preferably at least 9. Suitably, said pH is at most 12, more suitably at most 10, most suitably at most 8. A suitable pH measurement method is ASTM D1287. This implies that in the present invention, the mixture resulting from contacting the carbon dioxide stream resulting from step iv), or the condensate stream, or the waste water stream resulting from step v) with the alkali metal containing basic compound has a pH that is greater than 7, preferably at least 7.5, more preferably at least 8, more preferably at least 8.5, most preferably at least 9, and suitably at most 12, more suitably at most 10, most suitably at most 8.

Suitable examples of said alkali metal containing basic compound comprise potassium carbonate ($K_2CO_3$), potassium bicarbonate ($KHCO_3$), potassium hydroxide (KOH), sodium carbonate ($Na_2CO_3$), sodium bicarbonate ($NaHCO_3$) and sodium hydroxide (NaOH). Preferably, said alkali metal containing basic compound is potassium carbonate, potassium bicarbonate and/or potassium hydroxide. It is particularly preferred that the catalyst used in ethylene carbonate hydrolysis step iv) is also used as said alkali metal containing basic compound with which the carbon dioxide stream resulting from step iv) or the condensate stream is contacted.

Preferably, in the present invention, promoting the conversion of 2-iodoethanol or 2-bromoethanol into alkali metal iodide or alkali metal bromide and at the same preventing or reducing the conversion of 2-chloroethanol into alkali metal chloride, through contacting with the alkali metal containing basic compound, may be achieved by varying one or more of a variety of parameters. For example, said parameters comprise temperature, residence time (reaction time), reactant concentration (concentration of 2-chloroethanol and 2-iodoethanol or 2-bromoethanol), catalyst concentration and type of catalyst. Regarding the type of catalyst, e.g. KOH is more reactive than $KHCO_3$.

In the present invention, the temperature during contacting the carbon dioxide stream resulting from step iv), or the condensate stream, or the waste water stream resulting from step v) with the alkali metal containing basic compound may vary within wide ranges and may be of from 20 to 200° C., preferably 40 to 170° C., more preferably 50 to 150° C. Further, in the present invention, the time period of contacting the carbon dioxide stream resulting from step iv), or the condensate stream, or the waste water stream resulting from step v) with the alkali metal containing basic compound may also vary within wide ranges and may be of from 0.1 second to 5 hours, preferably 0.5 second to 2 hours, more preferably 1 to 30 minutes. Said time period is herein also referred to as residence time (reaction time).

In one embodiment of the present process (hereinafter "first embodiment"), the carbon dioxide stream resulting from step iv) is contacted in the condenser with an alkali metal containing basic compound, and the condensate stream comprising water, 2-chloroethanol and ethylene glycol and additionally comprising alkali metal iodide or alkali metal bromide is dehydrated. A condensed liquid is formed in the condenser which is contacted with the alkali metal containing basic compound in the condenser. An example of the first embodiment is illustrated in FIG. 1, as further described hereinbelow.

Preferably, in the first embodiment the condensate stream is dehydrated in step v). However, alternatively, the condensate stream may be dehydrated in another dehydration column, other than the dehydration column used in step v), to form a dehydrated ethylene glycol stream and a waste water stream, wherein the latter dehydrated ethylene glycol stream and the dehydrated ethylene glycol stream resulting from step v) may both be purified in step vi).

Further, preferably, in the first embodiment the condensate stream is dehydrated in step v) and is fed to the dehydration column at a position which is above the position at which the ethylene glycol stream is fed. Preferably, the condensate stream is fed at a position which is at least 1 stage, more preferably at least 2 stages, more preferably at least 3 stages, most preferably at least 5 stages, above the position at which the ethylene glycol stream is fed. In such way, contact between 2-chloroethanol from the condensate stream and catalyst from the ethylene glycol stream is advantageously avoided, thereby preventing formation of inorganic chloride (e.g. potassium chloride).

Further, preferably, in the first embodiment the temperature during contacting the carbon dioxide stream resulting from step iv) with the alkali metal containing basic compound in the condenser is of from 20 to 200° C., more preferably 20 to 150° C., more preferably 50 to 150° C., most preferably 80 to 150° C. The temperature of the stream is reduced in the condenser going from the upstream end (e.g. 150° C.) to the downstream end (e.g. 20° C.). The residence time in a condenser is generally in the order of seconds. At a relatively high temperature (e.g. 150° C.) the residence time in the condenser may be short, for example 0.5 to 1 second, whereas the residence time in the condenser at a lower temperature may be set longer. Furthermore, not only the residence time in the condenser is relevant, but also the residence time in a pipeline through which the condensate stream is sent to the dehydration column. Thus, the desired residence time for converting the 2-iodoethanol or 2-bromoethanol into alkali metal iodide or alkali metal bromide may be achieved through the design of the condenser and/or the design of the pipeline to the dehydration column.

Figure 2:
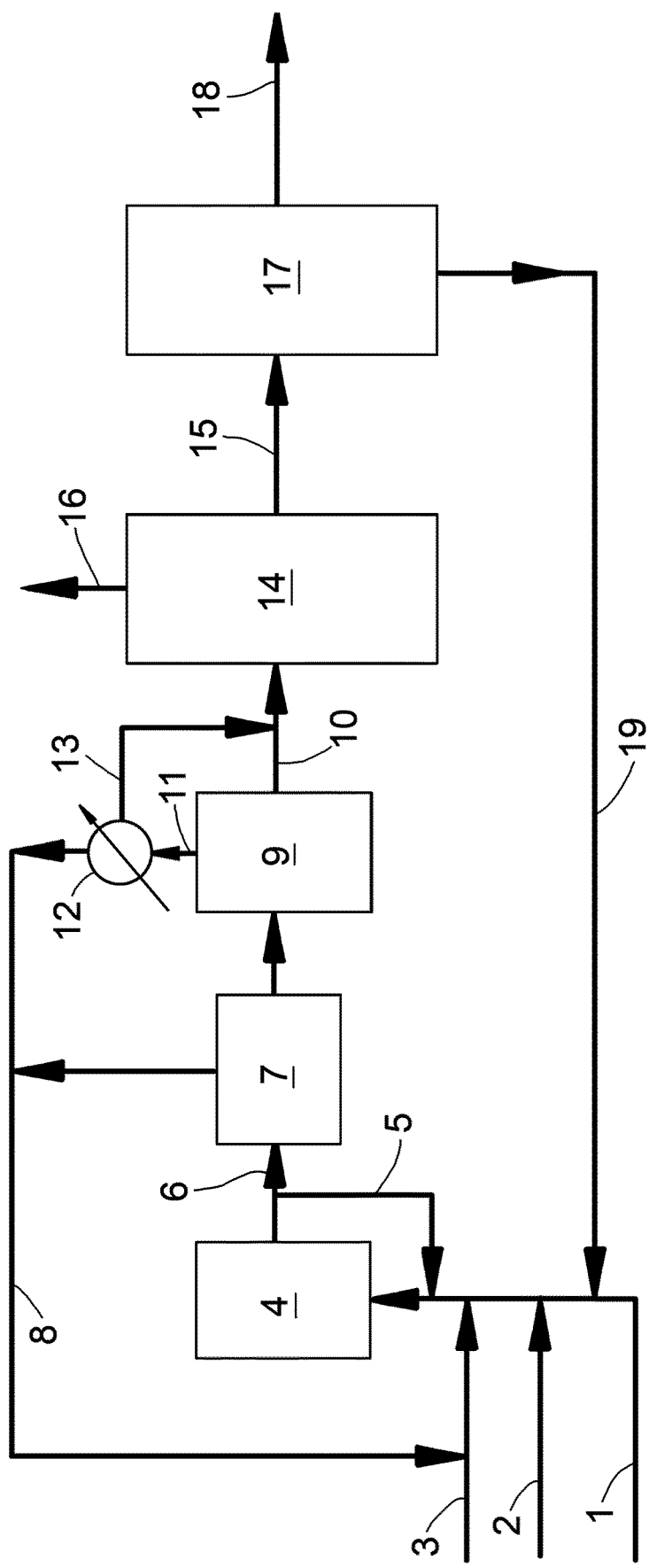

In another embodiment of the present process (hereinafter "second embodiment"), the ethylene glycol stream comprises an alkali metal containing basic compound, and the condensate stream comprises water, 2-chloroethanol and ethylene glycol and additionally comprises 2-iodoethanol or 2-bromoethanol and is contacted with the ethylene glycol stream, and the resulting ethylene glycol stream comprising water, 2-chloroethanol and ethylene glycol and additionally comprising alkali metal iodide or alkali metal bromide is fed to and dehydrated in step v). In the second embodiment, said contacting may be performed by in-line mixing or mixing in a separate vessel. An example of the second embodiment is illustrated in FIG. 2, as further described hereinbelow.

Preferably, in the second embodiment the temperature during contacting the condensate stream with the alkali metal containing basic compound containing ethylene glycol stream is of from 20 to 200° C., more preferably 60 to 180° C., more preferably 100 to 170° C., more preferably 120 to 160° C., most preferably 130 to 150° C. In the second embodiment, the latter temperature may be relatively high as generally the volume of the ethylene glycol stream having a relatively high temperature is significantly larger than the condensate stream having a relatively low temperature. In view of such relatively high contact temperature, it is preferred to keep the residence time relatively short. In the second embodiment, the residence time may be of from 0.1 second to 10 minutes, preferably 0.5 second to 5 minutes, more preferably 0.5 to 30 seconds, most preferably 0.5 to 5 seconds. For example, in the second embodiment, the residence time may be shortened by starting to mix the condensate stream with the ethylene glycol stream at a point which is at a relatively short distance upstream from the point where the resulting mixed stream is fed to the dehydration column used in step v).

Figure 3:
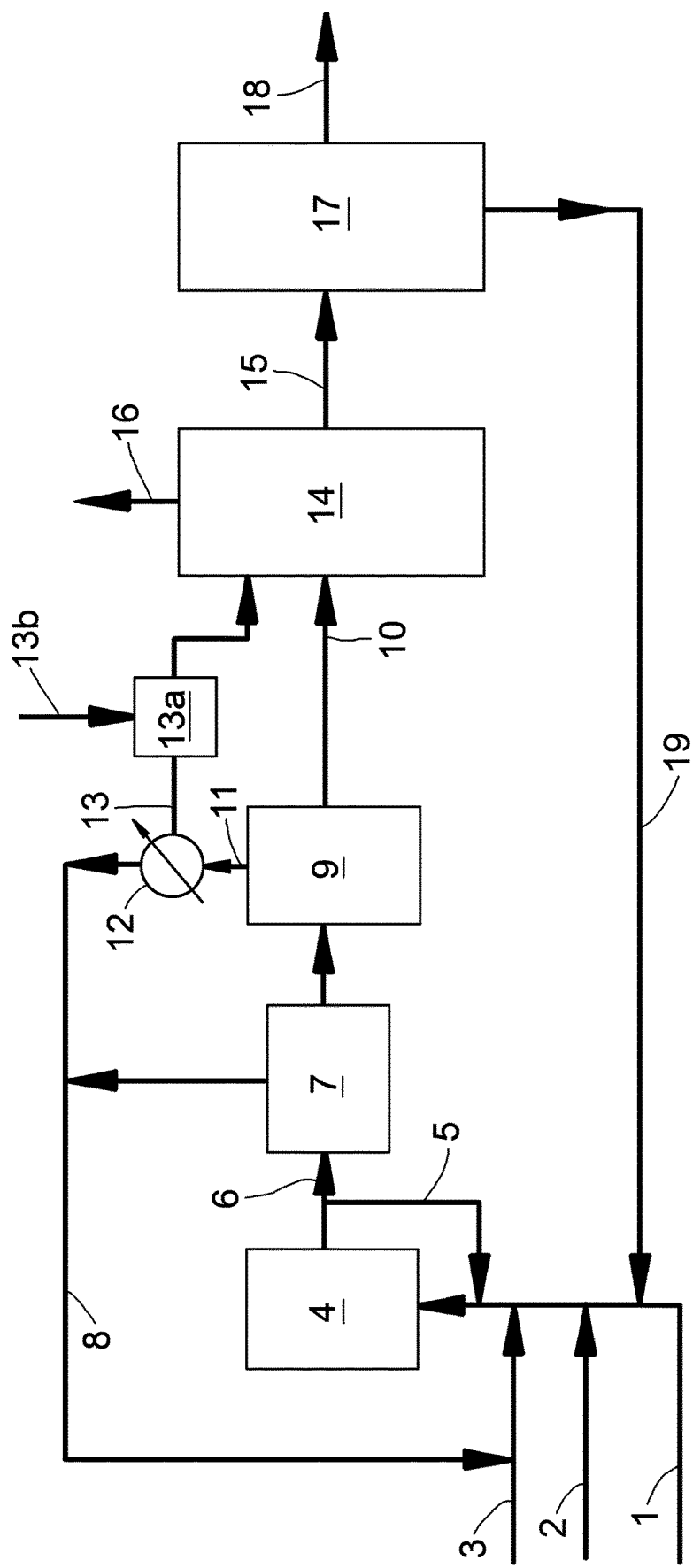

In yet another embodiment of the present process (hereinafter "third embodiment"), the condensate stream comprises water, 2-chloroethanol and ethylene glycol and additionally comprises 2-iodoethanol or 2-bromoethanol and is contacted with an alkali metal containing basic compound, and the resulting condensate stream comprising water, 2-chloroethanol and ethylene glycol and additionally comprising alkali metal iodide or alkali metal bromide is dehydrated. Preferably, in the third embodiment, the condensate stream is contacted with a stream comprising the alkali metal containing basic compound, which stream contains no or substantially no ethylene glycol. In the third embodiment, said contacting is performed before dehydration. In the third embodiment, said contacting may be performed by in-line mixing or mixing in a separate vessel. An example of the third embodiment is illustrated in FIG. 3, as further described hereinbelow.

Preferably, in the third embodiment the resulting condensate stream is dehydrated in step v). However, alternatively, the resulting condensate stream may be dehydrated in another dehydration column, other than the dehydration column used in step v), to form a dehydrated ethylene glycol stream and a waste water stream, wherein the latter dehydrated ethylene glycol stream and the dehydrated ethylene glycol stream resulting from step v) may both be purified in step vi).

Further, preferably, in the third embodiment the resulting condensate stream is dehydrated in step v) and is fed to the dehydration column at a position which is above the position at which the ethylene glycol stream is fed. Preferably, the resulting condensate stream is fed at a position which is at least 1 stage, more preferably at least 2 stages, more preferably at least 3 stages, most preferably at least 5 stages, above the position at which the ethylene glycol stream is fed. In such way, contact between 2-chloroethanol from the resulting condensate stream and catalyst from the ethylene glycol stream is advantageously avoided, thereby preventing formation of inorganic chloride (e.g. potassium chloride).

Further, in the third embodiment (i) the temperature during contacting the condensate stream with the alkali metal containing basic compound and (ii) the residence time may be varied within wide ranges. In general, it is preferred to combine a relatively high temperature with a relatively short residence time, and vice versa it is preferred to combine a relatively low temperature with a relatively long residence time. For example, in the third embodiment, said temperature may be of from 20 to 90° C., suitably of from 40 to 80° C., more suitably of from 60 to 80° C., in which case said residence time may be of from 10 to 30 minutes. Further, in case a relatively more reactive alkali metal containing basic compound is used, it is generally preferred to keep the residence time relatively short.

Still further, in a case wherein in the present process the waste water stream resulting from step v) is contacted with an alkali metal containing basic compound, the condensate stream comprises water, 2-chloroethanol and ethylene glycol and additionally comprises 2-iodoethanol or 2-bromoethanol and is preferably fed to and dehydrated in step v) to form a dehydrated ethylene glycol stream and a waste water stream. Preferably, in this case, the condensate stream is fed to the dehydration column in step v) at a position which is above the position at which the ethylene glycol stream is fed. Preferably, the condensate stream is fed at a position which is at least 1 stage, more preferably at least 2 stages, more preferably at least 3 stages, most preferably at least 5 stages, above the position at which the ethylene glycol stream is fed. In such way, contact between 2-chloroethanol from the condensate stream and catalyst from the ethylene glycol stream is advantageously avoided, thereby preventing formation of inorganic chloride (e.g. potassium chloride). In said case, the waste water stream comprises water and 2-chloroethanol and additionally comprises 2-iodoethanol or 2-bromoethanol. The waste water stream is condensed in a condenser resulting in a condensed liquid. The condensed liquid may be contacted with the alkali metal containing basic compound in the condenser. Or the condensate stream from the condenser may be contacted with the alkali metal containing basic compound, for example by in-line mixing or mixing in a separate vessel, preferably before splitting of the condensate stream into a bleed stream and a reflux stream that is sent back to the top of the dehydration column. The mixture resulting from contacting said waste water stream with an alkali metal containing basic compound comprises water, 2-chloroethanol and ethylene glycol and additionally comprises alkali metal iodide or alkali metal bromide. The latter mixture, in particular the mixture in said bleed stream, is preferably first separated, for example by distillation, into a stream comprising water and 2-chloroethanol and a stream comprising water, ethylene glycol and additionally comprising alkali metal iodide or alkali metal bromide. The latter stream is preferably recycled to and dehydrated in step v). Said stream may be recycled to the dehydration column in step v) at any position.

Step i) of the present process comprises converting ethylene in the presence of oxygen, an epoxidation catalyst and a chloride moderator to ethylene oxide in an ethylene oxide reactor.

The ethylene is reacted with oxygen in the presence of an epoxidation catalyst in a reactor to produce a gas composition comprising ethylene oxide, ethylene, oxygen, carbon dioxide and water vapour. The oxygen may be supplied as oxygen or as air, but is preferably supplied as oxygen. Ballast gas, for example methane or nitrogen, is typically supplied to allow operation at high oxygen levels without causing a flammable mixture.

A chloride moderator is supplied for catalyst performance control. Preferably, in the present invention, the chloride moderator is an organic compound containing 1 to 4, preferably 2 to 3, more preferably 2 carbon atoms, and one or more chlorine atoms. Said chloride moderator may be monochloroethane, dichloroethane or vinyl chloride.

The ethylene, oxygen, ballast gas and moderator are preferably supplied to recycle gas that is supplied to the ethylene oxide reactor from the ethylene oxide absorber (optionally via a carbon dioxide absorption column).

The ethylene oxide reactor is typically a multitubular, fixed bed reactor. The epoxidation catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C. The gas composition from the ethylene oxide reactor is preferably cooled in one or more coolers, preferably with generation of steam at one or more temperature levels.

Contaminants are preferably removed from the gas composition before it is supplied to the ethylene oxide absorber. Possible contaminants include acids, esters, aldehydes, acetals and organic halides. A preferred method of removing contaminants is quenching, preferably by contacting the gas composition with a cooled recirculating aqueous solution. Despite such a step, the gas composition supplied to the ethylene oxide absorber will contain organic chloride contaminants originating from the moderator used in the catalytic oxidation reaction.

Step ii) of the present process comprises absorbing the ethylene oxide in an aqueous absorbent and then stripping said absorbent to provide an aqueous ethylene oxide stream.

The gas composition from the oxidation step is supplied to an ethylene oxide absorber preferably comprising a column of vertically stacked trays or comprising a packed column.

Aqueous absorbent is supplied to the ethylene oxide absorber and is contacted with the gas composition in the ethylene oxide absorber. Typically the absorbent supplied to the ethylene oxide absorber is known as lean absorbent, and the stream leaving the ethylene oxide absorber (having absorbed ethylene oxide, carbon dioxide and light ends) is known as fat absorbent.

The lean absorbent suitably comprises at least 50 wt. % water. Preferably, the lean absorbent comprises at least 80 wt. % water.

The fat absorbent withdrawn from the absorber is supplied to a stripper. An aqueous ethylene oxide stream is produced from the top of the stripper. The remaining absorbent, now lean absorbent, is recycled to the ethylene oxide absorber.

The aqueous ethylene oxide stream from the top of the stripper suitably contains at least 50 wt. % ethylene oxide, preferably at least 55 wt. %. In certain embodiments, a stripper-concentrator is used, wherein the top product from the stripper is further concentrated. In these embodiments, the aqueous ethylene oxide stream may contain at least 95 wt. % ethylene oxide. In these embodiments, the aqueous ethylene oxide stream is diluted with water before being provided to the ethylene oxide to ethylene glycol section of the process.

Step iii) of the present process comprises converting the aqueous ethylene oxide stream in the presence of a catalyst and carbon dioxide in a carboxylation reactor to an ethylene carbonate stream.

In ethylene carbonate production step iii) of the present process, the catalyst may be an iodide catalyst or a bromide catalyst.

The above-mentioned iodide catalyst may be an alkali metal iodide or a phosphonium or ammonium iodide. The alkali metal in said alkali metal iodide may be any alkali metal and may be lithium, sodium, potassium, rubidium or cesium, preferably lithium, sodium or potassium, more preferably sodium or potassium. Most preferably, said alkali metal is potassium. Thus, most preferably, said alkali metal iodide is potassium iodide. Further, said phosphonium or ammonium iodide may be selected from the group consisting of tributylmethylphosphonium iodide, tetrabutylphosphonium iodide, triphenylmethylphosphonium iodide and tributylmethylammonium iodide. Preferably, said phosphonium or ammonium iodide is tributylmethylphosphonium iodide.

Further, the above-mentioned bromide catalyst may be an alkali metal bromide or a phosphonium or ammonium bromide. The alkali metal in said alkali metal bromide may be any alkali metal and may be lithium, sodium, potassium, rubidium or cesium, preferably lithium, sodium or potassium, more preferably sodium or potassium. Most preferably, said alkali metal is potassium. Thus, most preferably, said alkali metal bromide is potassium bromide. Further, said phosphonium or ammonium bromide may be selected from the group consisting of triphenylpropylphosphonium bromide, tetraethylammonium bromide, tetramethylammonium bromide, benzyltriethylammonium bromide and tetrabutylammonium bromide.

The aqueous ethylene oxide stream is provided to the ethylene oxide to ethylene glycol section of the process and is supplied to one or more carboxylation reactors. Carbon dioxide and a catalyst stream are also provided. The carbon dioxide and catalyst streams may be provided to the carboxylation reactor(s) separately from the aqueous ethylene oxide stream. Preferably, the carbon dioxide and catalyst streams are combined with the aqueous ethylene oxide stream prior to the aqueous ethylene oxide stream being supplied to the carboxylation reactor(s).

The catalyst stream comprises one or more catalysts that promote carboxylation and hydrolysis. If only one catalyst is present, then the catalyst must promote carboxylation and hydrolysis. If two or more catalysts are present, then each catalyst can promote carboxylation or hydrolysis or can promote both reactions (provided that at least one catalyst promotes carboxylation and at least one catalyst promotes hydrolysis).

In the present invention, the one or more catalysts that promote carboxylation and hydrolysis is/are homogeneous. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenylpropylphosphonium bromide, tetraethylammonium bromide, tetramethylammonium bromide, benzyltriethylammonium bromide, tetrabutylammonium bromide and tributylmethylammonium iodide. Homogeneous catalysts that are known to promote hydrolysis include basic alkali metal salts such as potassium carbonate, potassium hydroxide and potassium bicarbonate, or alkali metal metalates such as potassium molybdate.

Preferred homogeneous catalyst systems include a combination of tributylmethylphosphonium iodide and potassium carbonate, and a combination of potassium iodide and potassium carbonate.

The catalyst stream may be supplied to the carboxylation reactor either separately or after mixing with the aqueous ethylene oxide and/or $CO_2$ streams. After carboxylation, hydrolysis and dehydration, it is separated from the product stream in the catalyst separation section of the glycol distillation column. As the process of the present invention proceeds, a catalyst recycle stream from the catalyst separation section may be recycled to the carboxylation step.

Carboxylation of the aqueous ethylene oxide stream in the presence of carbon dioxide to produce an ethylene carbonate stream occurs in one or more carboxylation reactors. If more than one reactor is present, they are preferably arranged in series.

The carboxylation reactors are suitably two-phase flow reactors operating at a pressure in the range of from 0.8 to 3.0 MPa and a temperature in the range of from 50 to 180° C.

The carboxylation reactors will preferably each be provided with a recycle wherein liquid is removed from the reactor and then recycled to the bottom of the reactor. The recycle stream can be heated or cooled in order to provide improved temperature control to the carboxylation reactor.

Some hydrolysis may have occurred in the carboxylation reactors such that the ethylene carbonate stream will comprise some ethylene glycol.

After the aqueous ethylene oxide stream is converted to an ethylene carbonate stream in the one or more carboxylation reactors, the ethylene carbonate stream is then converted to an ethylene glycol stream in one or more hydrolysis reactors.

However, in a preferred embodiment of the process of the present invention, prior to being supplied to the one or more hydrolysis reactors, the ethylene carbonate stream is subjected to a carbon dioxide separation step in a carbon dioxide separation vessel. In this step, carbon dioxide is removed from the stream comprising the ethylene carbonate and the carbon dioxide may then be recycled to the carbon dioxide stream to be supplied to the carboxylation reactor.

Step iv) of the present process comprises converting the ethylene carbonate stream in the presence of a catalyst in a hydrolysis reactor to an ethylene glycol stream and a carbon dioxide stream resulting from step iv).

In ethylene carbonate hydrolysis step iv) of the present process, the catalyst may be a basic alkali metal salt such as potassium carbonate, potassium hydroxide and potassium bicarbonate, or an alkali metal metalate such as potassium molybdate, as described hereinabove with respect to step iii). Preferably, the hydrolysis catalyst is a basic alkali metal salt, in particular potassium carbonate.

Further, in step iv), the catalyst may be an iodide or bromide catalyst. Such iodide or bromide catalyst may be a catalyst as described hereinabove with respect to step iii).

The latter iodide or bromide catalyst may be one of two or more catalysts.

The one or more hydrolysis reactors may be any suitable reactor type. Preferably, the hydrolysis reactors are baffled reactors. If there is more than one hydrolysis reactor it is preferred that the hydrolysis reactors are connected in series.

In one embodiment of the invention, at least one of the one or more hydrolysis reactors is a baffled reactor, wherein the baffled reactor has at least 3, preferably at least 4 compartments, the compartments are formed by internal baffles and the internal baffles provide a sinuous route for reaction fluid through the reactor. Optionally, steam is injected into the baffled reactor.

Carbon dioxide is produced in the one or more hydrolysis reactors and is separated from the product stream as it leaves the one or more hydrolysis reactors as a carbon dioxide stream. In the present invention, the carbon dioxide stream resulting from step iv) is condensed in a condenser to form a recycle carbon dioxide stream and a condensate stream.

Said recycle carbon dioxide stream may be recycled to the carboxylation reactor.

The temperature in the one or more hydrolysis reactors is typically from 100 to 200° C., preferably from 100 to 180° C. The pressure in the one or more hydrolysis reactors is typically from 0.1 to 3 MPa.

Step v) of the present process comprises removing water from the ethylene glycol stream in a dehydration column to form a dehydrated ethylene glycol stream and a waste water stream. The waste water stream comprises water and 2-chloroethanol. Additionally, it may comprise chloromethyl dioxolane.

In step v), one or more dehydration columns may be used, which may include at least one vacuum column, preferably operating at a pressure of less than 0.05 MPa, more preferably less than 0.025 MPa and most preferably about 0.0125 MPa.

Step vi) of the present process comprises purifying the dehydrated ethylene glycol stream in a glycol distillation column to form a purified ethylene glycol product stream and a catalyst recycle stream. The catalyst recycle stream comprises ethylene glycol and catalyst including alkali metal iodide or alkali metal bromide, and may be recycled to the carboxylation reactor. In step vi), one or more glycol distillation columns may be used.

In the process shown in FIG. 1, an aqueous ethylene oxide stream (1) from the ethylene to ethylene oxide part of the process wherein a chloride moderator is used (not shown), is mixed with water (2), a catalyst stream (19) and carbon dioxide (3) before being supplied to a carboxylation reactor (4). Aqueous ethylene oxide stream (1) comprises water, ethylene oxide and 2-chloroethanol. Catalyst stream (19) comprises an iodide catalyst (carboxylation catalyst) and potassium carbonate (hydrolysis catalyst).

Carboxylation reactor (4) has a recycle (5). The ethylene carbonate stream (6) originating from carboxylation reactor (4) comprises carbon dioxide, water, ethylene carbonate, 2-chloroethanol, 2-iodoethanol and catalyst. Ethylene carbonate stream (6) is passed to a carbon dioxide separation vessel (7). Excess carbon dioxide is recycled via a recycle stream (8). The ethylene carbonate stream is then fed into a hydrolysis reactor (9), where it is converted to an ethylene glycol stream (10) and a carbon dioxide stream (11). Ethylene glycol stream (10) comprises water, ethylene glycol and catalyst. Carbon dioxide stream (11) comprises carbon dioxide, water, 2-chloroethanol, 2-iodoethanol and ethylene glycol.

Carbon dioxide stream (11) is condensed in a condenser (12) to form a recycle carbon dioxide stream and a condensate stream (13). Said recycle carbon dioxide stream is recycled via recycle stream (8). Potassium carbonate (an alkali metal containing basic compound) is fed via line (12a) to condenser (12) to convert 2-iodoethanol into potassium iodide. Condensate stream (13) comprises water, 2-chloroethanol, potassium iodide and ethylene glycol and is fed to a dehydrator (14) at a position which is above the position at which ethylene glycol stream (10) is fed.

Ethylene glycol stream (10) and condensate stream (13) are then dehydrated in dehydrator (14) to provide a dehydrated ethylene glycol stream (15) and a waste water stream (16). Dehydrated ethylene glycol stream (15) comprises ethylene glycol and catalyst including potassium iodide. Waste water stream (16) comprises water and 2-chloroethanol.

Dehydrated ethylene glycol stream (15) is purified in a glycol distillation column (17) to provide a purified ethylene glycol product stream (18) and a catalyst recycle stream (19). Catalyst recycle stream (19) comprises catalyst including potassium iodide and is recycled to carboxylation reactor (4).

The process as shown in FIG. 2 is the same as the process as shown in FIG. 1 with the following differences. Potassium carbonate is not fed to condenser (12). Condensate stream (13) comprises water, 2-chloroethanol, 2-iodoethanol and ethylene glycol and is combined with ethylene glycol stream (10) which comprises potassium carbonate (an alkali metal containing basic compound) to convert 2-iodoethanol into potassium iodide, and the resulting ethylene glycol stream comprising water, 2-chloroethanol, potassium iodide and ethylene glycol is fed to dehydrator (14).

The process as shown in FIG. 3 is the same as the process as shown in FIG. 1 with the following differences. Potassium carbonate is not fed to condenser (12). Condensate stream (13) is fed to a vessel (13a) and contacted with potassium carbonate (an alkali metal containing basic compound), which is fed to vessel (13a) via line (13b), to convert 2-iodoethanol into potassium iodide, and the resulting condensate stream comprising water, 2-chloroethanol, potassium iodide and ethylene glycol is fed to dehydrator (14) at a position which is above the position at which ethylene glycol stream (10) is fed.

The invention is further illustrated by the following Examples.

EXAMPLES

The following abbreviations are used: MEG=monoethylene glycol; DEG=diethylene glycol; CE=2-chloroethanol (MW=80.51 g/mole); IE=2-iodoethanol (MW=171.97 g/mole); KOH=potassium hydroxide (alkali metal containing basic compound); KCl=potassium chloride; KI=potassium iodide; ppmw=parts per million by weight.

In the experiment, a hydrolysis reaction product mixture comprising 94.7 wt. % of MEG, 5.0 wt. % of DEG and 39 mmol/kg of KOH was placed in a vessel at ambient temperature. A condensate stream comprising 81.3-83.0 wt. % of water, 14.2-15.9 wt. % of MEG, 2.4 wt. % of ethylene carbonate, 170-300 ppmw of CE and 110-160 ppmw of IE was mixed, by in-line mixing, with a hydrolysis reaction product stream from said vessel. The temperature of both said streams was ambient temperature. The relative amounts of the components in the condensate stream varied over time because different batches of the condensate stream were made for the experiments.

The resulting mixed stream was then fed to a distillation column at stage 12. The pipeline from the vessel to said column had a length of 5 m, and the condensate stream was mixed with the hydrolysis reaction product stream, in a weight ratio of 1:10, at a point which was at a distance of 4 m upstream of the column inlet, resulting in a residence time in the pipeline of about 60 minutes. In the last meter upstream of the column inlet, the mixed stream was heated by heat-tracing at 60° C. Said distillation column was a glass Oldershaw distillation column with 15 theoretical stages. The numbering of the stages starts at the bottom of the column. In the column, the bottom temperature was 137° C. and the bottom pressure was 110 mbara (82 torr). The temperature profile in the column was as follows: bottom: 137° C.; stage 4: 106° C.; stage 8: 62° C.; stage 12: 52° C.; top: 47° C. The distillation in the column resulted in an aqueous top stream and a bottom stream. The bottom stream was recycled to the above-mentioned vessel. Said bottom stream cooled down during flowing to said vessel.

The top stream from the distillation column comprised water, 100-400 ppmw of MEG, 300-320 ppmw of CE and 10-20 ppmw of IE. The bottom stream from the distillation column did not comprise CE and IE but comprised MEG, KI the amount of which increased over time from 0 to 2.5 mmol/kg (measured by titration as iodide ion I⁻), KOH the amount of which decreased over time from 39 to 10 mmol/kg, and KCl the amount of which increased over time from 0 to 2.2 mmol/kg (measured by titration as chloride ion Cl⁻).

The total duration of the experiment was 840 hours, and samples of said top and bottom streams were taken and analysed daily. In Table 1 below, experimental results at running the process for 792 hours are included.

TABLE 1

|  | Condensate stream | Top stream |
| --- | --- | --- |
| Total flow rate (g/h) | 15.1 | 13.5 |
| Amount of CE (ppmw) | 287 | 307 |
| CE flow rate (mmole/h) = A | 0.054 | 0.052 |
| Amount of IE (ppmw) | 110 | 12.7 |
| IE flow rate (mmole/h) = B | 0.0096 | 0.0010 |
| % of CE in top stream [100*$A_{top}/A_{cond}$] |  | 96.2% |
| % of IE in top stream [100*$B_{top}/B_{cond}$] |  | 10.4% |

Surprisingly, the results in Table 1 above show that a relatively large portion (96.2%) of the CE fed to the process left the process via the top stream from the distillation column, whereas only a relatively small portion (10.4%) of the IE fed left the process via said top stream. This means that, since the bottom stream from the distillation column did not comprise IE, a relatively large portion (89.6%) of the IE fed was advantageously converted into MEG and KI by contacting and reacting it with KOH. Indeed, as described above, said bottom stream comprised an increasing amount of KI and a decreasing amount of KOH.

In summary, these experiments demonstrated that surprisingly most of the IE reacted with KOH into KI and additional MEG, as shown (i) by a relatively small amount of IE in the top stream and (ii) by an increase of the KI amount and a decrease of the KOH amount in the bottom stream. On the contrary, advantageously, most of the CE was removed from the process via said top stream and was therefore not converted into KCl. Said KI may be recycled and advantageously be used as a catalyst in carboxylation (making ethylene carbonate) and/or hydrolysis (making MEG).

That we claim:

1. A process for the preparation of ethylene glycol from ethylene involves:
   i) converting ethylene in the presence of oxygen, an epoxidation catalyst and a chloride moderator to ethylene oxide in an ethylene oxide reactor;
   ii) absorbing the ethylene oxide in an aqueous absorbent and then stripping said absorbent to provide an aqueous ethylene oxide stream;
   iii) converting the aqueous ethylene oxide stream in the presence of a catalyst and carbon dioxide in a carboxylation reactor to an ethylene carbonate stream;

iv) converting the ethylene carbonate stream in the presence of a catalyst in a hydrolysis reactor to an ethylene glycol stream and a carbon dioxide stream;

v) removing water from the ethylene glycol stream in a dehydration column to form a dehydrated ethylene glycol stream and a waste water stream;

vi) purifying the dehydrated ethylene glycol stream in a glycol distillation column to form a purified ethylene glycol product stream and a catalyst recycle stream;

wherein in step iii) and/or step iv) the catalyst is an iodide catalyst or a bromide catalyst;

the carbon dioxide stream resulting from step iv) comprises carbon dioxide, water, 2-chloroethanol and ethylene glycol and additionally comprises 2-iodoethanol or 2-bromoethanol and is condensed in a condenser to form a recycle carbon dioxide stream and a condensate stream; and the carbon dioxide stream resulting from step iv), or the condensate stream, or the waste water stream resulting from step v) is contacted with an alkali metal containing basic compound to convert 2-iodoethanol or 2-bromoethanol into alkali metal iodide or alkali metal bromide and the resulting mixture comprising water, 2-chloroethanol and ethylene glycol and additionally comprising alkali metal iodide or alkali metal bromide is dehydrated.

2. The process according to claim 1, wherein the temperature during contacting the carbon dioxide stream resulting from step iv), or the condensate stream, or the waste water stream resulting from step v) with the alkali metal containing basic compound is of from 20 to 200 ° C.

3. The process according to claim 1 wherein the time period of contacting the carbon dioxide stream resulting from step iv), or the condensate stream, or the waste water stream resulting from step v) with the alkali metal containing basic compound is of from 0.1 second to 5 hours.

4. The process according to claim 1, wherein the carbon dioxide stream resulting from step iv) is contacted in the condenser with an alkali metal containing basic compound, and the condensate stream comprising water, 2-chloroethanol and ethylene glycol and additionally comprising alkali metal iodide or alkali metal bromide is dehydrated.

5. The process according to claim 4, wherein the condensate stream is dehydrated in step v) and is fed to the dehydration column at a position which is above the position at which the ethylene glycol stream is fed.

6. The process according to claim 1, wherein the ethylene glycol stream comprises an alkali metal containing basic compound, and the condensate stream comprises water, 2-chloroethanol and ethylene glycol and additionally comprises 2-iodoethanol or 2-bromoethanol and is contacted with the ethylene glycol stream, and the resulting ethylene glycol stream comprising water, 2-chloroethanol and ethylene glycol and additionally comprising alkali metal iodide or alkali metal bromide is fed to and dehydrated in step v).

7. The process according to claim 1, wherein the condensate stream comprises water, 2-chloroethanol and ethylene glycol and additionally comprises 2-iodoethanol or 2-bromoethanol and is contacted with an alkali metal containing basic compound, and the resulting condensate stream comprising water, 2-chloroethanol and ethylene glycol and additionally comprising alkali metal iodide or alkali metal bromide is dehydrated.

8. The process according to claim 7, wherein the resulting condensate stream is dehydrated in step v) and is fed to the dehydration column at a position which is above the position at which the ethylene glycol stream is fed.

\* \* \* \* \*